(12) United States Patent
Hallen

(10) Patent No.: US 12,685,670 B2
(45) Date of Patent: Jul. 21, 2026

(54) LASER VITRECTOMY AND BLEEDING CESSATION TOOL

(71) Applicant: Alcon Inc., Fribourg (CH)

(72) Inventor: Paul R. Hallen, Colleyville, TX (US)

(73) Assignee: Alcon Inc., Fribourg (CH)

( * ) Notice: Subject to any disclaimer, the term of this patent is extended or adjusted under 35 U.S.C. 154(b) by 121 days.

(21) Appl. No.: 18/434,470

(22) Filed: Feb. 6, 2024

(65) Prior Publication Data

US 2024/0261141 A1     Aug. 8, 2024

Related U.S. Application Data

(60) Provisional application No. 63/483,776, filed on Feb. 8, 2023.

(51) Int. Cl.
    *A61F 9/007* (2006.01)
    *A61F 9/008* (2006.01)
(52) U.S. Cl.
    CPC ...... *A61F 9/00763* (2013.01); *A61F 9/00709* (2013.01); *A61F 9/008* (2013.01); *A61F 2009/00874* (2013.01)
(58) Field of Classification Search
    CPC .. A61F 9/00763; A61F 9/00709; A61F 9/008; A61F 2009/00874; A61F 9/00821; A61F 9/00736
    See application file for complete search history.

(56) References Cited

U.S. PATENT DOCUMENTS

| | | | | |
|---|---|---|---|---|
| 4,122,853 | A * | 10/1978 | Smith ................. | B23K 26/064 |
| | | | | 606/4 |
| 7,566,173 | B2 | 7/2009 | Auld et al. | |
| 9,782,232 | B1 | 10/2017 | Papac | |
| 10,238,543 | B2 | 3/2019 | Farley | |
| 10,307,290 | B2 | 6/2019 | Kern | |
| 10,463,533 | B2 | 11/2019 | Charles | |
| 10,478,266 | B2 * | 11/2019 | Mirsepassi ......... | A61F 9/00736 |
| 11,160,686 | B2 | 11/2021 | Cook et al. | |
| 11,213,426 | B2 | 1/2022 | Cook et al. | |
| 11,331,219 | B2 | 5/2022 | Farley | |
| 11,622,885 | B2 | 4/2023 | Meckel | |
| 2010/0228238 | A1 * | 9/2010 | Brennan .............. | A61B 5/0073 |
| | | | | 600/476 |
| 2012/0041461 | A1 * | 2/2012 | McCollam ............. | A61B 90/30 |
| | | | | 606/170 |
| 2013/0150839 | A1 | 6/2013 | Smith | |

(Continued)

FOREIGN PATENT DOCUMENTS

WO         2023012531 A1     2/2023

*Primary Examiner* — David Hamaoui
*Assistant Examiner* — Olivia Walker

(57) ABSTRACT

The present disclosure generally relates to a surgical instrument. The surgical instrument includes a base unit and a probe. The probe is disposed through an opening in a distal end of the base unit. The probe includes a port formed proximate to a distal tip of the probe. The distal tip includes a window, a lumen formed through the probe, and one or more optical fibers disposed in the lumen. The one or more optical fibers project a first laser light for irradiating an area proximate to the port to cut collagen fibers of vitreous material aspirated through the port. The one or more optical fibers further project a second laser light for cauterizing bleeding in an intraocular space of a patient.

19 Claims, 5 Drawing Sheets

(56)               References Cited

U.S. PATENT DOCUMENTS

| | | |
|---|---|---|
| 2017/0014187 A1 | 1/2017 | Wang et al. |
| 2018/0368911 A1 | 12/2018 | Van Overdam |
| 2019/0201238 A1 | 7/2019 | Bacher et al. |
| 2021/0290438 A1* | 9/2021 | Hallen ................ A61F 9/00736 |
| 2022/0401261 A1* | 12/2022 | Lambert ................ A61B 17/30 |
| 2023/0165714 A1 | 6/2023 | Hallen |

* cited by examiner

LASER VITRECTOMY AND BLEEDING CESSATION TOOL

BACKGROUND

Anatomically, the human eye is divided into two distinct regions—the anterior segment and the posterior segment. The anterior segment includes the lens and extends from the outermost layer of the cornea to the posterior of the lens capsule. The posterior segment of the eye includes the anterior hyaloid membrane and all of the ocular structures behind it, such as the vitreous humor, retina, choroid, and the optic nerve.

Vitreoretinal procedures are commonly performed within the posterior segment of the human eye to treat serious conditions such as age-related macular degeneration (AMD), macular holes, premacular fibrosis, retinal detachment, epiretinal membrane, cytomegalovirus (CMV) retinitis, diabetic retinopathy, vitreous hemorrhages, and other ophthalmic conditions. Such procedures frequently require the severance and removal of portions of the vitreous humor from the posterior segment of the eye, which is a colorless and gel-like substance that makes up approximately two-thirds of the eye's volume. In a vitrectomy procedure, a surgeon inserts microsurgical instruments through one or more incisions made in the eye to sever and remove the vitreous body from within.

The microsurgical instruments typically utilized during a vitrectomy include a vitrectomy probe for severing and removing the vitreous body from the intraocular space. During a vitrectomy procedure, it is possible that bleeding of the retina can occur as a result of vitreoretinal traction caused during the severance and removal of the vitreous. Bleeding can increase intraocular pressure (IOP), or the fluid pressure within the eye, thereby creating further issues during the procedure. In order to stop the bleeding, a diathermy needle can be used to cauterize the bleeding site on the retinal surface. However, to use a diathermy needle, the surgeon must first remove the microsurgical instrument being used to sever/remove the vitreous, thereby complicating and reducing the overall efficiency of the procedure. Further, the cauterized tissue can stick to the metal tip of the diathermy needle, which can re-open the bleeding site. Thus, a more efficient was to stop bleeding during a vitrectomy procedure is needed.

SUMMARY

The present disclosure generally relates to microsurgical instruments for ophthalmic surgical procedures, and more particularly, microsurgical instruments having combined laser vitrectomy and cauterization functions.

In one embodiment, a surgical instrument is provided. The surgical instrument includes a base unit and a probe. The probe is disposed through an opening in a distal end of the base unit. The probe includes a port formed proximate to a distal tip of the probe. The distal tip includes a window, a lumen formed through the probe, and one or more optical fibers disposed in the lumen. The one or more optical fibers project a first laser light for irradiating an area proximate to the port to cut collagen fibers of vitreous material aspirated through the port. The one or more optical fibers further project a second laser light for cauterizing bleeding in an intraocular space of a patient.

In another embodiment, a surgical instrument is provided. The surgical instrument includes a base unit and a probe. The probe is disposed through an opening in a distal end of the base unit. The probe includes a port formed proximate to a distal tip of the probe, a lumen formed through the probe, and one or more optical fibers disposed in the lumen. The optical fibers project a first laser light for irradiating an area proximate to the port to cut collagen fibers of vitreous material aspirated through the port. The one or more optical fibers further project a second laser light for cauterizing bleeding in an intraocular space of a patient. The distal tip comprises a window configured to allow the second laser light to pass through the distal tip and prevent the first laser light from passing through the distal tip.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

The present disclosure generally relates to microsurgical instruments for ophthalmic surgical procedures, and more particularly, to microsurgical instruments having combined laser vitrectomy and cauterization functions.

In some embodiments, a surgical instrument includes a base and a probe having a main lumen and a port at a distal tip thereof. In some embodiments, the probe may further include a single optical fiber within the main lumen, the single optical fiber configured to project both a first laser light as well as a second laser light. According to some embodiments, when (e.g., as soon as) vitreous material is drawn into the probe (e.g., through the port) during an ophthalmic surgical procedure, the vitreous material passes through a volume proximate to the port as the volume is irradiated by the first laser light emitted by the optical fiber, thus severing the vitreous material. The severed vitreous material may then be aspirated out of the eye and proximally through the probe. Additionally, in the event of bleeding during the surgical procedure, the optical fiber may emit an alternative wavelength of light (e.g., the second laser light) in order to cauterize the bleeding site.

In some other embodiments, separate optical fibers may be used for projecting the first laser light and the second laser light. For example, in such embodiments, a first optical fiber may be used for projecting a first laser light to sever the vitreous material, and a second optical fiber may be used for projecting a second laser light to cauterize the bleeding site.

Figure 1:
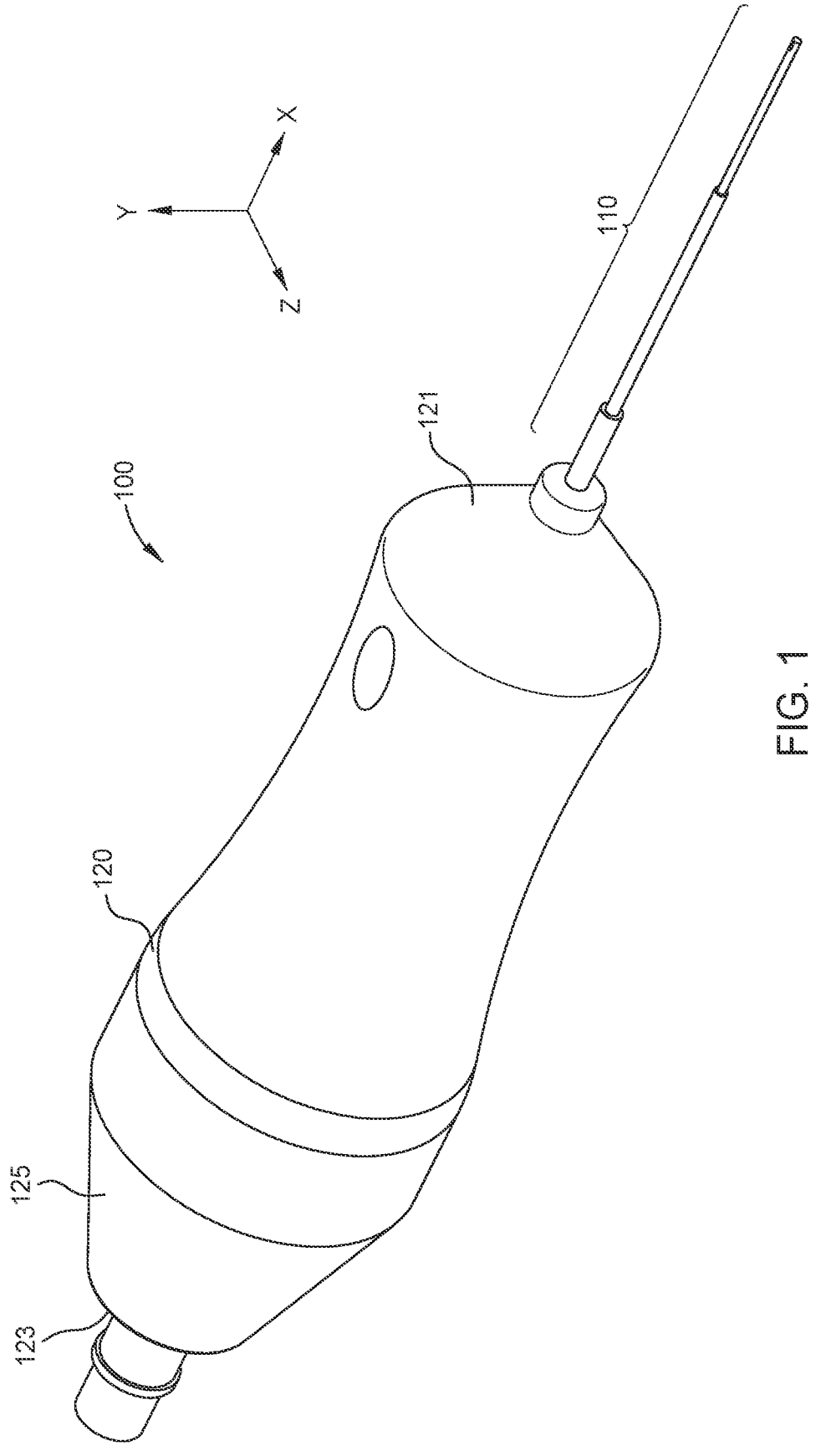
FIG. 1 illustrates a perspective view of an exemplary surgical instrument, according to some embodiments of the present disclosure.

FIG. 1 illustrates a perspective view of an exemplary surgical instrument 100, according to certain embodiments described herein. As depicted in FIG. 1, the surgical instrument 100 comprises a probe 110 and a base unit 120. The probe 110 is partially and longitudinally disposed through a distal end 121 of the base unit 120 and may be directly or indirectly attached thereto within an interior chamber of the base unit 120. Note that, as described herein, a distal end or portion of a component refers to the end or the portion that is closer to a patient's body during use thereof. On the other hand, a proximal end or portion of the component refers to the end or the portion that is distanced further away from the patient's body.

In some embodiments, the base unit 120 is a hand piece having an outer surface configured to be held by a user, such as a surgeon. For example, the base unit 120 may be ergonomically contoured to substantially fit the hand of the user. In some embodiments, the outer surface may be textured or have one or more gripping features formed thereon, such as one or more grooves and/or ridges. The base unit 120 may be made from any materials commonly used for such instruments and suitable for ophthalmic surgery. For example, the base unit 120 may be formed of a light-weight aluminum, a polymer, or other suitable material. In some embodiments, the base unit 120 may be sterilized and used in more than one surgical procedure, or it may be a single-use device.

The base unit 120 further provides one or more ports 123 (e.g., one port 123 is depicted in FIG. 1) at a proximal end 125 thereof for one or more supply lines to be routed into an interior chamber of the base unit 120. For example, the port 123 may provide a connection between the base unit 120 and a vacuum line of a vacuum source for aspiration. The port 123 may also provide a connection to an optical fiber cable that couples to one or more light sources for providing laser light.

Figure 2A:
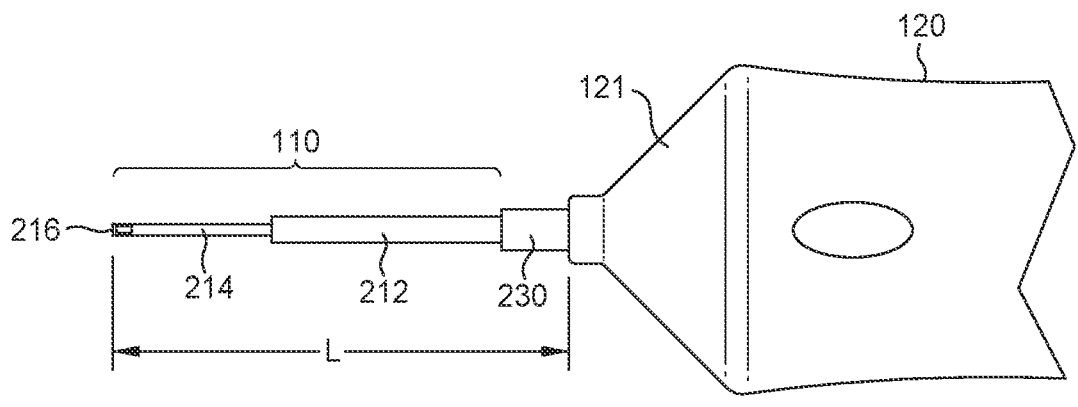
FIG. 2A illustrates a plan view of a portion of the surgical instrument of FIG. 1, according to some embodiments of the present disclosure.

FIG. 2A illustrates a plan view of the probe 110 and the distal end 121 of the base unit 120. As shown, the probe 110 may be an elongated laser-based cutting member that may be inserted into an eye, e.g., through an insertion cannula, for performing vitrectomy, which may be aspirating or non-aspirating. The probe 110 may thus be formed of materials suitable for minimally invasive vitreoretinal surgeries. For example, the probe 110 may include one or more sections formed of an opaque material, such as a plastic and/or polymeric material. The probe 110 may further include one or more sections formed of more surgical-grade materials, such as stainless steel and/or aluminum.

In certain embodiments, the probe 110 has a length L between about 15 mm (millimeters) and about 30 mm, but may have a larger or smaller length in some embodiments. The probe 110 may comprise a hollow tube having an outer diameter less than about 20 gauge. In some embodiments, the probe 110 is segmented into two or more portions (e.g., regions or segments) having outer diameters of differing sizes. For example, as shown in FIG. 2A, the probe 110 may include a proximal portion 212 having a larger outer diameter than a distal portion 214 that terminates at a distal tip 216. In some embodiments, the proximal portion 212 has an outer diameter of about 23 gauge and the distal portion 214 has an outer diameter of about 25 gauge.

In some embodiments, the proximal portion 212 has an outer diameter of about 25 gauge and the distal portion 214 has an outer diameter of about 27 gauge. In some other embodiments, the proximal portion 212 has an outer diameter of about 27 gauge and the distal portion 214 has an outer diameter of about 29 gauge. In some embodiments, the proximal portion 212 functions as an infusion portion and is configured to direct infusion fluid into the operating space adjacent the probe during use thereof. The proximal portion 212 may thus include one or more coaxial infusion ports concentrically disposed around the distal portion 214 and fluidly connected to a fluid source through the base unit 120. Delivery of infusion fluid to the interior eye during vitreoretinal surgery enables the maintenance of intraocular pressure (IOP), thereby preventing the eye from collapsing during the surgical procedure.

In some embodiments, the surgical instrument 100 further includes a stiffener 230 fixedly or slidably coupled to and substantially surrounding at least a portion of the probe 110. For example, the stiffener 230 is slidably coupled to an exterior surface 236 (shown in FIGS. 2B-2C) of the probe 110 and may extend from and retract into the base unit 120. The stiffener 230 may be adjustable relative to the probe 110, enabling a user to position the stiffener 230 at different points along a length L of the probe 110 exterior to the base unit 120. Accordingly, a user may selectively adjust the level of stiffness of the probe 110 by re-positioning the stiffener 230 relative to the distal tip 216, thereby manipulating the amount of support provided to the probe 110 and stabilizing the surgical instrument 100 during use thereof.

As described above, in some embodiments, the surgical instrument 100 provides a single optical fiber that is configured to project a multiple wavelengths of laser light. Various examples of using a single optical fiber for projecting multiple wavelengths of laser light are depicted in FIGS. 2B, 20, 4A, and 4B. In some other embodiments, one or more optical fibers may be used for projecting a first laser light while one or more additional optical fibers may be used for projecting a second laser light. Various examples of using multiple fibers for projecting a first laser light and a second laser light are depicted in FIGS. 3 and 5A-5C.

Figure 2B:
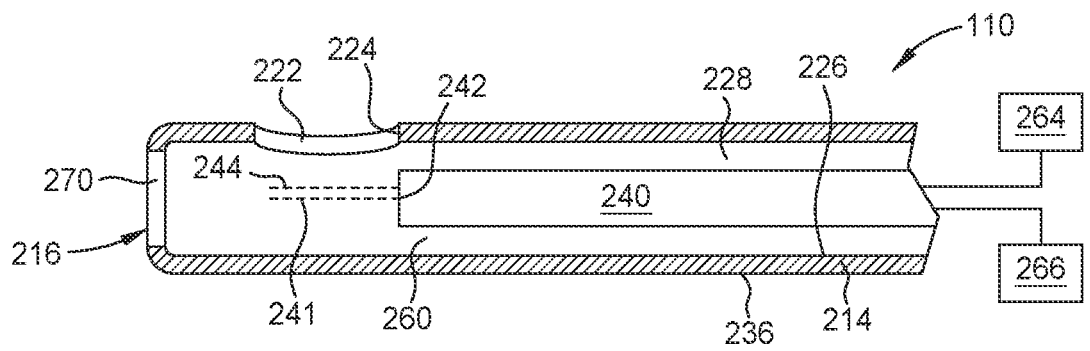
FIG. 2B illustrates a stylized longitudinal cross-sectional view of a portion of the surgical instrument, according to some embodiments of the present disclosure.
Figure 2C:
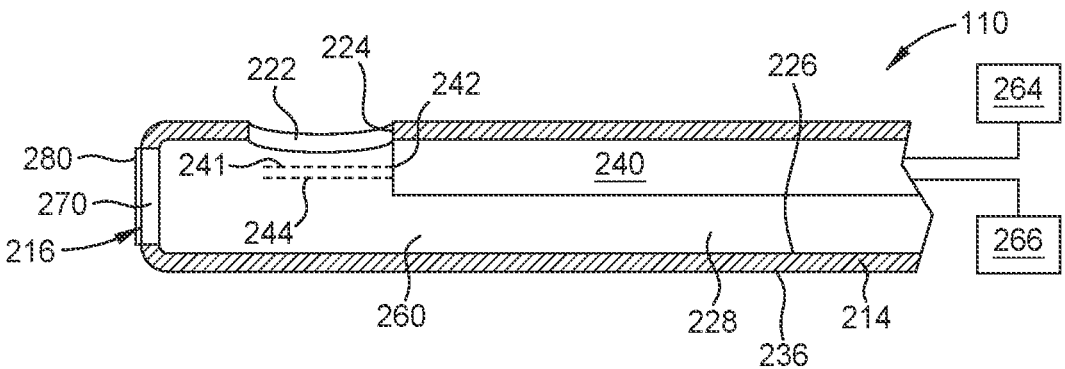
FIG. 2C illustrates another stylized longitudinal cross-sectional view of a portion of the surgical instrument, according to some embodiments of the present disclosure.

FIGS. 2B and 2C illustrate stylized longitudinal cross-sectional views of the distal portion 214 of the probe 110 having the optical fiber 240 housed therein. As depicted, the probe 110 includes a main lumen 260 and a port 222 near (e.g., proximate to) the distal tip 216. In one example, the main lumen 260 has a substantially circular cross section. The port 222, which is located at the distal tip 216 of the distal portion 214, is sized and shaped to allow vitreous collagen fibers to enter the main lumen 260 during vitrectomy. In some examples, the vitreous collagen fibers may be aspirated into the main lumen 260 through the port 222. As further described below, the optical fiber 240 is configured to project a first laser light 241 to sever the vitreous fibers that enter the port 222.

In the embodiments of FIGS. 2B and 2C, the distal tip 216 comprises a flat tip. In other words, the distal tip 216 is disposed at an angle normal to a longitudinal central axis of the probe 110. However, other arrangements of the distal tip 216 are further contemplated, such as that depicted and described with reference to FIG. 3.

The optical fiber 240 may be designed to operate as an optical waveguide and propagate the first laser light 241 through a terminal end 242 thereof. The characteristics of the first laser light 241 propagated through the optical fiber 240 are such that the first laser light 241 causes disruption of the vitreous collagen fibers within the path of the first laser light 241. Disruption refers to the breaking down of the tissue by rapid ionization of molecules thereof. In some examples, the first laser light 241 may be produced by a first laser light source 264 optically coupled to the optical fiber 240 using an optical fiber cable, as described above. In some embodiments, the first laser light 241 propagated by the optical fiber 240 is an ultraviolet ("UV") (<350 nm (nanometers)) laser light. In other embodiments, the first laser light 241 is an argon blue-green laser light (488 nm), a Nd-YAG laser light (532 nm) such as a frequency-doubled Nd-YAG laser light, a krypton red laser light (647 nm), a diode laser light (805-810 nm), or any other suitable type of laser light for ophthalmic surgery.

In some embodiments, the first laser light source 264 may produce a first laser light 241 having a pulse rate within a range of about 10 kilohertz (kHz) and about 500 kHz. This range of pulse rate can effectively provide disruption of the vitreous body. Other pulse rate ranges can also provide disruption and are thus contemplated as well. In some examples, the first laser light source 264 produces a picosecond or femtosecond first laser light 241. In some embodiments, the first laser light source 264 may produce a continuous coherent first laser light 241. For example, the first laser light source 264 may produce a continuous coherent first laser light 241 at low power.

In certain embodiments, the optical fiber 240 is disposed within the main lumen 260 and terminates at the terminal end 242 near the port 222 such that the first laser light 241 projecting from the optical fiber 240 will be projected across the port 222 with sufficient power to sever vitreous collagen fibers. In the embodiment depicted in FIG. 2B, the optical fiber 240 is rigidly suspended within the main lumen 260 such that the optical fiber 240 is separated from an interior sidewall 226 of the probe 110 and the optical fiber 240 is circumferentially surrounded by a space 228. The space 228 formed between the optical fiber 240 and the interior sidewall 226 of the probe 110 provides a coaxial path for aspiration of severed vitreous collagen fibers through the probe 110. In some embodiments, the optical fiber 240 may be centrally disposed within the main lumen 260 such that a radial distance between the interior sidewall 226 and the optical fiber 240 is uniform along a circumference of the optical fiber 240.

In the embodiment depicted in FIG. 2C, the optical fiber 240 may be disposed along (e.g., coupled to) the interior sidewall 226. For example, the optical fiber 240 may be coupled to the interior sidewall 226 along a longitudinal length thereof. In some embodiments, the optical fiber 240 is coupled to the interior sidewall 226 along a portion of the interior sidewall 226 radially aligned with the port 222 such that the terminal end 242 of the optical fiber 240 terminates at a point radially inward of the port 222 relative to a longitudinal central axis of the probe 110. The optical fiber 240 may be coupled to the interior sidewall 226 with any suitable adhesive or bonding mechanism, such as an epoxy or acrylic adhesive.

The terminal end 242 of the optical fiber 240 may terminate at any point along the length L of the probe 110 to enable optimal severance of vitreous fibers, as well as aspiration of vitreous fiber thereof. In some embodiments, the terminal end 242 of the optical fiber 240 terminates within the main lumen 260 at a point distal to a proximal end 224 of the port 222. In other embodiments, the terminal end 242 of the optical fiber 240 terminates at a point within the main lumen 260 substantially aligned with the proximal end 224. In still other embodiments, the terminal end 242 of the optical fiber 240 terminates within the main lumen 260 at a point proximal to the proximal end 224.

In the embodiments of FIGS. 2B-2C, the optical fiber 240 is further configured to propagate a second laser light 244 in addition to and separate from the first laser light 241. For example, in certain embodiments, a second laser light source 266 may be used to provide the second laser light 244 to the optical fiber 240. In certain other embodiments, however, the second laser light 244 may be generated and provided to the optical fiber 240 via the first laser light source 264, which may be configured to generate both the first laser light 241 and the second laser light 244. The optical fiber 240 propagates the second laser light 244 in one of a variety of ways for facilitating cauterization of a bleeding site within the eye to prevent further bleeding during a surgical procedure.

The characteristics of the second laser light 244 propagated through the optical fiber 240 are such that the second laser light 244 may cause cauterization of a bleeding site, on the surface of the retina, inadvertently caused during the vitrectomy. Bleeding during surgery mainly occurs from inadvertent damage to vessels in the retina, such as by vitreoretinal traction, and is a serious complication during a vitrectomy. If not controlled immediately, such bleeding can prevent successful completion of surgery. In some examples, the second laser light 244 may be produced by the second laser light source 266 optically coupled to the optical fiber 240 using an optical fiber cable, as described above. In some embodiments, the second laser light 244 propagated by the optical fiber 240 is green laser light (497 nm-577 nm, e.g. 532 nm).

In some embodiments, the second laser light source 266 may produce a second laser light 244 having a pulse rate within a range of about 10 kilohertz (kHz) and about 500 KHz. This range can effectively cauterize bleeding within the eye without the using an additional microsurgical instrument (e.g., a metal diathermy tip), thus slowing down the procedure. Further, the second laser light 244 can cauterize the bleeding without tissue sticking to the metal diathermy tip, which can re-open the bleeding. Other pulse rate ranges can also provide cauterization and are thus contemplated as well. In some examples, the second laser light source 266 produces a picosecond or femtosecond second laser light 244. In some embodiments, the second laser light source 266 may produce a continuous coherent second laser light 244. For example, the second laser light source 266 may produce a continuous coherent second laser light 244 at low power.

In embodiments where a single optical fiber 240 is used for projecting both the first laser light 241 as well as the second laser light 244, the laser light sources may be configured to focus the first laser light 241 and second laser light 244 on a core of the optical fiber 240, and thus the first laser light 241 and second laser light 244 are transmitted through the core. In some embodiments, the second laser light source 266 is configured to focus the second laser light 244 onto both the core and a cladding of the optical fiber 240, in which case both the cladding and the core transmit the second laser light 244. In some embodiments, the first laser light source 264 is configured to focus the first laser light 241 onto both the core and a cladding of the optical fiber 240, in which case both the cladding and the core transmit the first laser light 241.

In yet some other embodiments, the second laser light source 266 is configured to focus the second laser light 244 onto just the core or the cladding, in which case only one of the core or the cladding transmit the second laser light 244. In yet some other embodiments, the first laser light source 264 is configured to focus the first laser light 241 onto just the core or the cladding, in which case only one of the core or the cladding transmit the first laser light 241. Thus, the optical fiber 240, including a core and a cladding, is capable of transmitting the first laser light 241 (through the cladding and/or the core) and the and second laser light 244 (through the cladding and/or the core) in the same fiber. In some embodiments, the first laser light 241 and second laser light 244 are propagated through one or more additional cores in the optical fiber 240. Thus, the optical fiber 240 may include one or more cores through which the first laser light 241 and second laser light 244 are separately propagated.

In some embodiments, the second laser light 244 is coaxially projected with the first laser light 241 from the terminal end 242 of the optical fiber 240. In certain embodiments, propagation of first laser light 241 and second laser light 244 through the optical fiber 240 and into the intraocular space may be modulated by utilizing different types of laser light sources, utilizing different materials for the optical fiber 240, modifying the physical arrangement of the optical fiber 240 within the probe 110, and/or by utilizing different materials for the probe 110.

In some embodiments, the first laser light 241 and second laser light 244 can be switched on or off, and/or the user can toggle between the first laser light 241 and the second laser light 243, using a foot pedal. In some embodiments, the first laser light 241 and the second laser light 244 can be switched on or off, and/or the user can toggle between the first laser light 241 and the second laser light 243, using a button or switch on the base unit 120.

In some embodiments, the optical fiber 240 has a diameter between about 20 μm (micrometers) and about 120 μm, such as a diameter between about 40 μm and about 100 μm. For example, the optical fiber 240 has a diameter between about 50 μm and about 80 μm. However, smaller or larger diameters are also contemplated. In some embodiments, a light sleeve assembly containing a plurality of optical fibers 240 is utilized. For example, a light sleeve containing a plurality of optical fibers 240 having uniform or different diameters may be utilized. In further embodiments, the optical fiber 240 is a multi-mode end-emitting fiber, a single-mode end-emitting fiber, or the like.

In some embodiments, as shown in FIGS. 2B and 2C, the distal tip 216 comprises a window 270. The window 270 may be configured to allow all wavelengths or some wavelengths of light to pass through the distal tip 216. In some embodiments, the window 270 is fabricated to only allow particular wavelengths of light to pass through the distal tip 216. For example, in FIG. 2B, the window 270 is configured to allow the second laser light 244 to pass through the distal tip 216, but is further configured to prevent the first laser light 241 from passing through the distal tip 216. By allowing only the second laser light 244 of the two laser lights 241, 244 to pass through the distal tip 216 of the probe 110, targeting and cauterization of bleeding sites within the eye is efficiently enabled, while also preventing unwanted transmission of the first laser light 241 through the distal tip 216 during performance of vitrectomy. Accordingly, the modified window 270 prevents unnecessary damage to the patient's eye during vitrectomy by containing the first laser light 241 within the probe 110, while also facilitating targeted cauterization through the distal tip 216.

In some embodiments, as shown in FIG. 2C, the window 270 may be fabricated to allow all wavelengths of light to pass through the distal tip 216, but may be fully or partially coated with a filtering film 280. The filtering film 280 may allow no wavelengths or only particular wavelengths of light to pass through the distal tip 216. For example, the filtering film 280 may be fabricated to allow the second laser light 244 to pass through the distal tip 216, but may be fabricated to prevent the first laser light 241 from passing through the distal tip 216. This facilitates cauterization of bleeding sites through the distal tip 216, while also preventing excessive damage to the eye during the vitrectomy by containing the first laser light 241 within the probe 110.

Figure 3A:
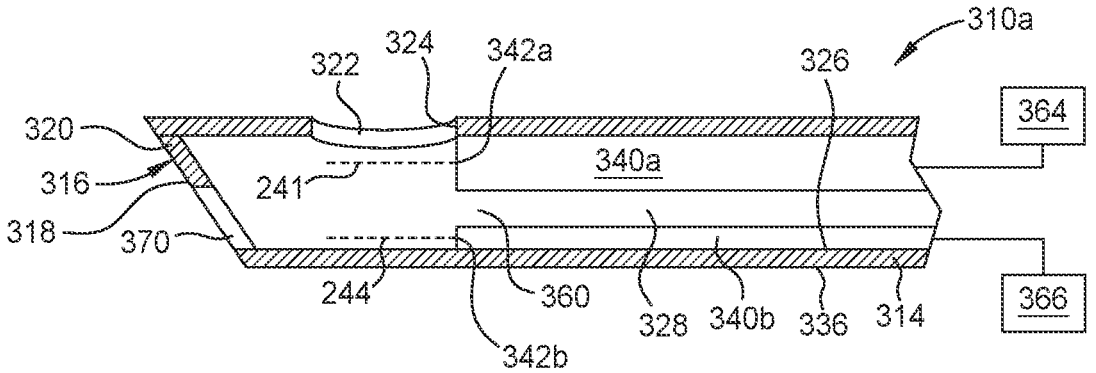
FIG. 3A illustrates a stylized longitudinal cross-sectional view of a portion of the surgical instrument of FIG. 1, according to some embodiments of the present disclosure.
Figure 3B:
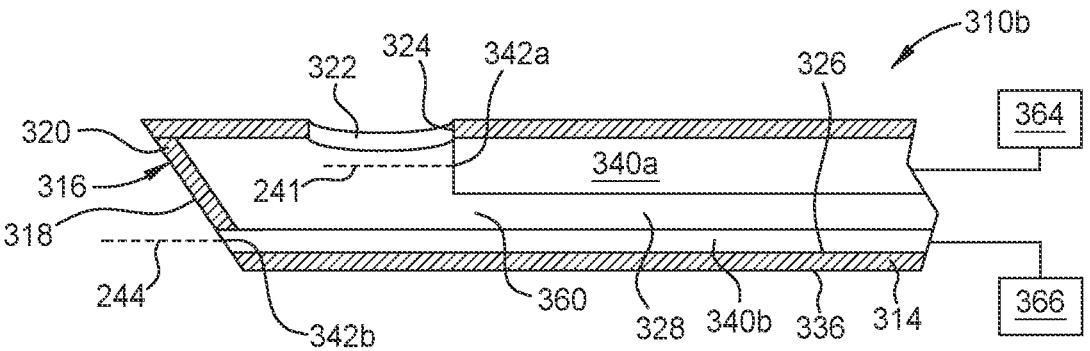
FIG. 3B illustrates another stylized longitudinal cross-sectional view of a portion of the surgical instrument, according to some embodiments of the present disclosure.

FIG. 3A illustrates a stylized longitudinal cross-sectional view of a distal portion 314 of an alternative probe 310a according to certain embodiments described herein. FIG. 3B illustrates a stylized longitudinal cross-sectional view of a distal portion 314 of an alternative probe 310b according to certain embodiments described herein. The alternative probes 310a, 310b are substantially similar to the probe 110, but further includes a beveled distal tip 316 and two optical fibers housed therein: a first optical fiber 340a and second optical fiber 340b. Similar reference numbers, therefore, are used to represent similar elements where applicable.

The beveled distal tip 316 may be beveled (e.g., disposed at a non-normal angle relative to a major axis (e.g., the longitudinal central axis) of the probe 110. For example, the beveled distal tip 316 may be disposed at an angle between about 0 and about 90 degrees relative to the longitudinal central axis of the probe 110. However, other arrangements of the distal tip 316 are further contemplated, such as those depicted and described with reference to FIGS. 2B and 2C.

Each of the optical fibers 340a and 340b of the probe 310a, 310b may be configured to transmit a different type and/or wavelength of laser light, as described elsewhere herein. For example, the optical fiber 340a in FIGS. 3A and 3B may be configured to transmit the first laser light 241, while the second optical fiber 340b may be configured to transmit the second laser light 244. In such embodiments, first optical fiber 340a may be disposed along (e.g., coupled to) the interior sidewall 326 and a second optical fiber 340b may be disposed along (e.g., coupled to) the interior sidewall 326 on the opposite side of the main lumen 360. In some embodiments, the second optical fiber 340b is coupled to the interior sidewall 326 along a portion of the interior sidewall 326 radially opposite to the port 322. The optical fibers 340a, 340b may be coupled to the interior sidewall 326 with any suitable adhesive or bonding mechanism, such as an epoxy or acrylic adhesive.

The terminal ends 342a, 342b of the optical fibers 340, 340b may terminate at any points along the length L of the probe 110 to enable optimal severance of vitreous fibers for vitrectomy and cauterization of bleeding sites, respectively, as well as aspiration of vitreous fiber and blood thereof. In some embodiments, the terminal ends 342a, 342b of the optical fibers 340*a* and/or 340*b* terminate within the main lumen 360 at a point distal to a proximal end 324 of the port 322. In other embodiments, as shown in FIG. 3A, the terminal ends 342*a*, 342*b* of the optical fibers 340*a*, 340*b* terminate at a point within the main lumen 360 substantially aligned with the proximal end 324. In still other embodiments, the terminal ends 342*a*, 342*b* of the optical fibers 340*a*, 340*b* terminate within the main lumen 360 at a point proximal to the proximal end 324. In certain embodiments, the terminal ends 342*a*, 342*b* of the optical fibers 340*a*, 340*b* terminate at a different points along the length L of the probe 110. For example, as shown in FIG. 3B, the terminal end 342*a* of the optical fiber 340*a* may terminate proximally or adjacent to proximal end 324, while the terminal end 342*b* of the optical fiber 340*b* may terminate distally to proximal end 324 (e.g., the terminal end 342*b* of the optical fiber 340*b* forms a portion of the distal end 316, as described below).

In some embodiments, the beveled distal tip 316 comprises the window 370, which may form all, or substantially all, of a distal endface 318 of the beveled distal tip 316 (e.g., the window 370 may span across an entire lateral width or diameter of the distal endface 318). The window 370 may be fabricated to allow all lights or particular wavelengths or light to pass through the beveled distal tip 316. In certain embodiments, the window 370 may be a modified window fabricated to allow only certain wavelengths of light to pass through the beveled distal tip 316. For example, the modified window 370 may be fabricated to allow the second laser light 244 to pass through the modified window 370 while simultaneously not allowing the first laser light 241 to pass through the modified window 370. In certain embodiments, the window 370 may be fabricated to allow all wavelengths of light to pass through the beveled distal tip 316, but may further be coated with a filtering film (e.g., filtering film 280 described above) across an entire lateral width or diameter of the window 370, or only a portion of the lateral width or diameter of the window 370. The filtering film may allow the second laser light 244 to pass through the modified window 370, while simultaneously not allowing the first laser light 241 to pass through the modified window 370. In certain embodiments, the filtering film 280 may cover only a portion of the lateral width or diameter of the window 370, such as a portion aligned with the optical fiber 340*a*, and may not allow any laser light to pass through. In such embodiments, the filtering film 280 may be opaque.

In still further embodiments, as shown in FIG. 3A, the window 370 may only partially form the distal endface 318 of the beveled distal tip 316. For example, in certain embodiments, a portion of the distal endface 318 comprises the window 370, while another portion of the distal endface 318 comprises a wall 320 formed of a probe material. The probe material may comprise an opaque material, such as a plastic and/or polymeric material. Meanwhile, the window 370 may be fabricated to allow all wavelengths of light to pass through, or only certain wavelengths of light to pass through, the beveled distal tip 316. Further, in certain embodiments, the window 370 may also be coated with a filtering film.

In embodiments where the window 370 only forms a portion of the distal endface 318, the window 370 is generally axially aligned with the optical fiber 340*b*, and the wall 320 is axially aligned with the first optical fiber 340*a*. Accordingly, the wall 320 prevents the passage of the first laser light 241 through the beveled distal tip 316 of the probe 310*a*, thus preventing the first laser light 241 from causing damage to the eye during performance of vitrectomy by containing the first laser light 241 within the probe 310*a*.

The window 370, however, allows the second laser light 244 to pass through the distal endface 318 for cauterization of bleeding sites within the eye. By allowing the second laser light 244 to pass through the beveled distal tip 316 of the probe 310*a*, the bleeding site can be easily targeted with the probe 310.

In still further embodiments, as shown in FIG. 3B, the wall 320 only partially forms the distal endface 318 of the beveled distal tip 316. For example, the wall 320 comprises the probe material that forms a portion of the distal enface 318, while another portion of the distal endface 318 of the beveled distal tip 316 is formed of the terminal end 342*b* of the optical fiber 340*b*. The probe material may comprise an opaque material, such as a plastic and/or polymeric material. In embodiments where the terminal end 342*b* of the optical fiber 340*b* forms a portion of the distal endface 318, the wall prevents the passage of the first laser light 241 through the beveled distal tip 316 of the probe 310*b*, thus preventing the first laser light 241 from causing damage to the eye during performance of vitrectomy by containing the first laser light 241 within the probe 310*b*. The endface 342*b*, however, allows the second laser light 244 to pass through the distal endface 318 for cauterization of bleeding sites within the eye. By allowing the second laser light 244 to pass through the beveled distal tip 316 of the probe 310*b*, the bleeding site can be easily targeted with the probe 310.

Figure 4A:
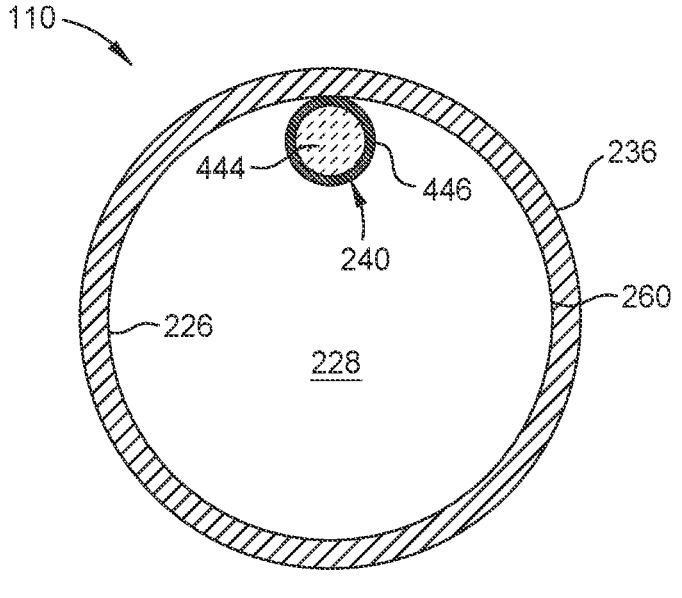
FIG. 4A illustrates a front sectional view of the exemplary surgical instrument of FIG. 1, according to some embodiments of the present disclosure.
Figure 4B:
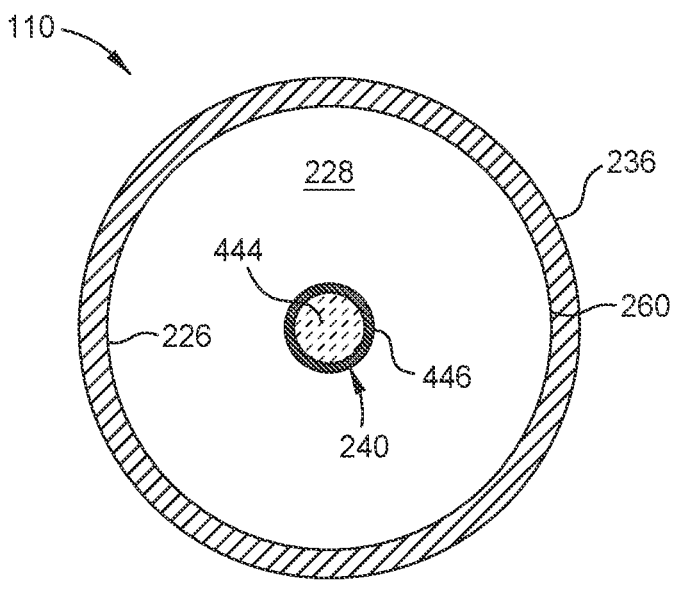
FIG. 4B illustrates another front sectional view of the exemplary surgical instrument, according to some embodiments of the present disclosure.

FIGS. 4A-4B illustrate exemplary front sectional views of the probe 110 of FIGS. 2A-2C having the single optical fiber 240 housed therein for projecting both the first laser light 241 and second laser light 244. As depicted, the probe 110 has a circular cross section defined by the interior sidewall 226 and the exterior surface 236. Generally, the optical fiber 240 includes a core 444 and a cladding 446 circumferentially surrounding the core 444 in accordance with embodiments of the present disclosure. The core 444 may comprise any transparent material, such as fused silica or glass. In some embodiments, the core 444 is doped. For example, the core 444 may be germanium-doped silica. Doping the core 444 with germanium or a similar dopant may increase the refractive index of the core 444 compared to that of the cladding 446 material, hence enabling laser and light guiding properties within the core 444.

The cladding 446 may also comprise a transparent material, such as fused silica or glass. In some embodiments, the cladding 446 is doped in addition to or instead of doping the core 444. For example, the cladding 446, which may comprise fused silica, is doped with a dopant that reduces the refractive index of the cladding 446 relative to that of the core 444. Example dopants include fluorine (F), chlorine (CI), boron (B), or the like. The cladding 446, when doped, has a lower refractive index than the core 444, thus enabling light guiding properties within the core 444. Although one cladding 446 is depicted in each of FIGS. 4A, 4B, the optical fiber 440 may further include one or more additional claddings.

In one example, the core 444 has a diameter in the range of 5 μm and about 100 μm, such as a diameter between about 20 μm and about 80 μm, such as a diameter of about 75 μm. However, smaller or larger diameters are also contemplated. In one example, the cladding 446 has a thickness between about 5 μm and about 50 μm, such as a thickness between about 15 μm and about 40 μm, such as a thickness of about 25 μm. However, smaller or larger thicknesses are also contemplated.

In some embodiments, the optical fiber 240 is disposed within a sleeve. The sleeve may couple directly or indirectly to an exterior of the cladding 446 and circumferentially surround the cladding 446 and the core 444 of the optical fiber 240 therewithin. The sleeve may act as a tubular structure for providing structural support and alignment of the optical fiber 240 within the main lumen 260 of the probe 110. Similar to the core 444 and the cladding 446, the sleeve may comprise a transparent material such as fused silica and glass. In further embodiments, the sleeve is doped with a dopant to manipulate the refractive index of the sleeve as desired.

FIG. 4A illustrates an arrangement wherein the optical fiber 240 is disposed against the interior sidewall 226 of the probe 110. The optical fiber 240 may be coupled to the interior sidewall 226 along a longitudinal portion thereof radially aligned with the port 222 (shown in FIGS. 2A-2C). Thus, the space 228 is formed within a main lumen 260 around the optical fiber 240 but for the longitudinal portion of the interior sidewall 226 to which the optical fiber 240 is coupled. The optical fiber 240 may be coupled or bonded to the interior sidewall 226 via any suitable adhesive or bonding mechanism. For example, an exterior surface 236 of the cladding 446 or the sleeve 448 may be bonded to the interior sidewall 226 of the probe 110 with an epoxy or acrylic adhesive. However, other adhesives are also contemplated.

FIG. 4B illustrates an alternative exemplary arrangement in which the optical fiber 240 is suspended within the main lumen 260. In some examples, the sleeve may provide structural support and rigidity to the optical fiber 240 to enable suspension of the optical fiber 240 inside the main lumen 260 without coupling the optical fiber 240 to the interior sidewall 226. As depicted in FIG. 4B, the optical fiber 240 may be centrally disposed within the main lumen 260 such that the radial distance between a point on an exterior surface of the optical fiber 240 and the interior sidewall 226 is uniform around the entire circumference of the optical fiber 240.

Figure 5A:
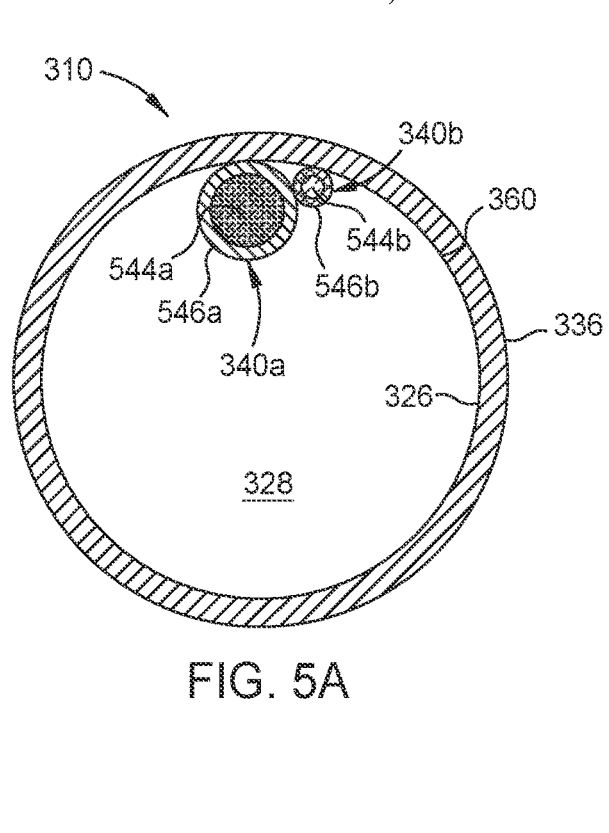
FIG. 5A illustrates a front sectional view of the exemplary surgical instrument of FIG. 1, according to some embodiments of the present disclosure.
Figure 5B:
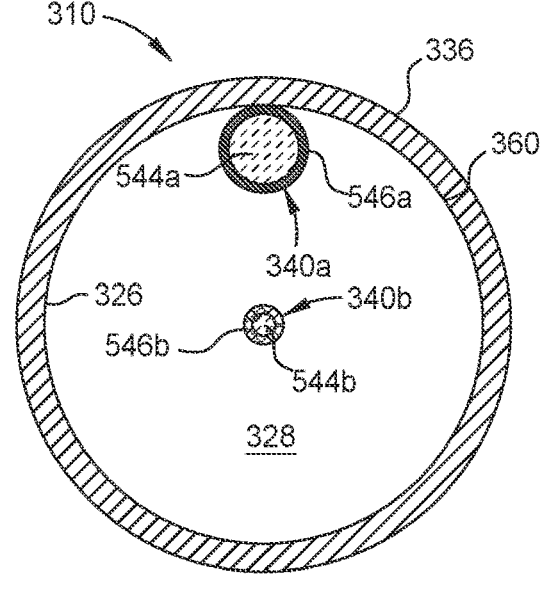
FIG. 5B illustrates another front sectional view of the exemplary surgical instrument, according to some embodiments of the present disclosure.
Figure 5C:
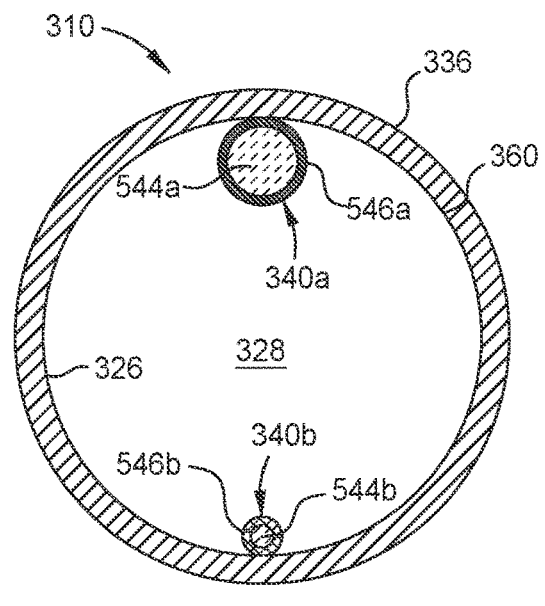
FIG. 5C illustrates another front sectional view of the exemplary surgical instrument, according to some embodiments of the present disclosure.

FIGS. 5A-5C illustrate exemplary front sectional views of the probe 310 having the at least two optical fibers 340a, 340b housed therein. As described above, the first optical fiber 340a may be utilized to propagate the first laser light 241 for vitreous fibril severance. Meanwhile, the second optical fiber 340b may be utilized to propagate the second laser light 244 for bleeding site cauterization. Each of the optical fibers 340a, 340b further includes a core 544a, 544b and a cladding 546a, 546b, respectively. The cores 544a, 544b and the claddings 546a, 546b may be formed of any suitable materials for propagation of laser light beams, respectively. For example, the cores 544a, 544b and the claddings 546a, 546b may comprise a transparent material such as fused silica or glass, as described above. The cores 544a, 544b and the claddings 546a, 546b may further be doped with one or more dopants depending on desired refractive properties for each of the optical fibers 340a, 340b.

The dimensions of the optical fibers 340a, 340b, including the cores 544a, 544b and claddings 546a, 546b, may be substantially similar to the dimensions of optical fiber 240, core 444, and cladding 446 described above. Although depicted as having different dimensions in FIGS. 5A-5C, the optical fibers 340a, 340b and the cores 544a, 544b and the claddings 546a, 546b may have similar or different dimensions to each other.

In some embodiments, the optical fibers 340a, 340b are both disposed within a secondary lumen of a sleeve. The sleeve may provide structural support and containment of the optical fibers 340a, 340b within the main lumen 360 of the probe 310. A sleeve may comprise a transparent material such as fused silica and glass. In further embodiments, the sleeve is doped with a dopant to manipulate the refractive index of the sleeve as desired. The sleeve may have any suitable thickness to provide appropriate support and rigidity to the optical fibers 340a, 340b. In some embodiments, a transparent filler material may be used within the secondary lumen to prevent movement of the optical fibers 340a, 340b within. For example, an adhesive may fill all areas within the secondary lumen that are not occupied by the optical fibers 340a, 340b. In other embodiments, the optical fibers 340a, 340b are disposed within the secondary lumen without the utilization of a filler material.

FIGS. 5A-5C illustrate exemplary arrangements of the optical fibers 340a, 340b without the utilization of the sleeve. In FIG. 5A, the optical fibers 340a, 340b are disposed within the main lumen 360 of the probe 310 without any surrounding structure other than the probe 310 itself.

In FIG. 5A, the optical fibers are coupled together and are further coupled to the interior sidewall 326. Thus, the space 328 is formed within a main lumen 360 around the optical fibers 340a, 340b but for the longitudinal portion of the interior sidewall 326 to which the optical fibers 340a, 340b are coupled. The optical fibers 340a, 340b may be coupled or bonded to the interior sidewall 326 via any suitable adhesive or bonding mechanism. For example, an exterior surface of the cladding 546a, 546b may be bonded to the interior sidewall 326 of the probe 310 with an epoxy or acrylic adhesive. However, other adhesives are also contemplated.

In FIGS. 5B and 5C, the optical fibers 340a, 340b may be separate and isolated from each other within the main lumen 360. In FIG. 5B, the optical fibers 340a, 340b are disposed within the main lumen 360 such that the first optical fiber 340a is coupled to the interior sidewall 326 and the second optical fiber 340b is suspended within the main lumen 360. In some examples, the sleeve may provide structural support and rigidity to the second optical fiber 340b to enable suspension of the second optical fiber 340b inside the main lumen 360 without coupling the second optical fiber 340b to the interior sidewall 326. The second optical fiber 340b may be centrally disposed within the main lumen 360 such that the radial distance between a point on an exterior surface 336 of the second optical fiber 340b and the interior sidewall 326 is uniform around the entire circumference of the second optical fiber 340b.

In FIG. 5C, the optical fibers 340a, 340b are disposed against the interior sidewall 326 of the probe 310. The optical fiber 340 may be coupled to the interior sidewall 326 along a longitudinal portion thereof radially aligned with the port 322. Thus, the space 328 is formed within a main lumen 360 around the optical fibers 340a, 340b but for the longitudinal portion of the interior sidewall 326 to which the optical fibers 340a, 340b are coupled. The optical fibers 340a, 340b may be coupled or bonded to the interior sidewall 326 via any suitable adhesive or bonding mechanism. For example, an exterior surface of the cladding 546a, 546b may be bonded to the interior sidewall 326 of the probe 310 with an epoxy or acrylic adhesive. However, other adhesives are also contemplated.

In some embodiments, the optical fibers 340a, 340b are placed through a spacer tube having one or more longitudinal bores drilled therethrough to allow placement of the optical fibers 340a, 340b. The spacer tube may act in a substantially similar manner to the sleeve and provide structural support and containment of the optical fibers 340a, 340b. The spacer tube may be formed of any suitable transparent materials, including fused silica and/or glass.

In summary, embodiments of the present disclosure include devices and structures for performing vitreoretinal surgery. In particular, the surgical instruments described above combine the functions of laser vitrectomy and intraocular cauterization, thus enabling more efficient performance of vitreous removal. Utilization of a first laser light from the vitrectomy probe allows the collagen fibers of vitreous material to be easily removed, which reduces retinal traction produced by removing the vitreous material. Furthermore, propagation of second laser light through the vitrectomy probe enables cauterization of intraocular bleeding without the need for a secondary cauterization device, which may provide inefficient cauterization or limit the operating room within the intraocular space. Still further, the embodiments described herein provide arrangements for controlling the dispersion of the first laser light and second laser light within the eye for a user of a vitrectomy probe, which allows for more accurate targeting of the second laser light for cauterization and prevents dispersion of the first laser light within the eye to prevent additional occurrences of bleeding. Accordingly, the described embodiments enable the performance of more efficient, less invasive, and safer vitreoretinal procedures.

Although vitreous surgery is discussed as an example of a surgical procedure that may benefit from the described embodiments, the advantages of the surgical devices and systems described herein may benefit other surgical procedures as well.

While the foregoing is directed to embodiments of the present disclosure, other and further embodiments of the disclosure may be devised without departing from the basic scope thereof, and the scope thereof is determined by the claims that follow.

What is claimed is:

1. A surgical instrument for performing vitrectomy, comprising:
   a base unit;
   a probe coupled to a distal end of the base unit, the probe comprising:
   a distal tip disposed at a distal end of the probe, the distal tip comprising a window;
   a port formed in a side wall of the probe and proximate to the distal tip;
   a lumen formed through the probe; and
   one or more optical fibers disposed in the lumen, the one or more optical fibers configured to project a first laser light for irradiating an area proximate to the port, wherein the first laser light is configured to cut collagen fibers of vitreous material aspirated through the port, the one or more optical fibers further configured to project a second laser light through the window, wherein the second laser light is configured to cauterize a bleeding site;
   wherein the window is configured to allow the second laser light to pass through the window and prevent the first laser light from passing through the window.

2. The surgical instrument of claim 1, wherein the one or more optical fibers comprise a single optical fiber configured to project the first laser light and the second laser light.

3. The surgical instrument of claim 2, wherein the window is spectrally selective to allow the second laser light to pass through the window and prevent the first laser light from passing through the window.

4. The surgical instrument of claim 1, wherein the window is coated with a filtering film configured to allow the second laser light to pass through the distal tip and prevent the first laser light from passing through the distal tip.

5. The surgical instrument of claim 1, wherein the one or more optical fibers comprise a first optical fiber configured to project the first laser light and a second optical fiber configured to project the second laser light.

6. The surgical instrument of claim 5, wherein the probe further comprises a distal endface disposed at the distal tip, and wherein the window forms a portion of the distal endface that is aligned with the second optical fiber such that the distal endface enables the second laser light to pass through the distal tip and prevents the first laser light from passing through the distal tip.

7. The surgical instrument of claim 6, wherein the window is coated in a filtering film configured to allow the second laser light to pass through the distal tip and prevent the first laser light from passing through the distal tip.

8. The surgical instrument of claim 6, wherein a portion of the window aligned with the first optical fiber is coated in an opaque film configured to prevent the first laser light and the second laser light from passing through the distal tip.

9. A surgical instrument for performing vitrectomy, comprising:
   a base unit;
   a probe disposed through an opening in a distal end of the base unit, the probe comprising:
   a distal tip comprising a window;
   a port formed proximate to the distal tip;
   a lumen formed through the probe; and
   one or more optical fibers disposed in the lumen, the one or more optical fibers configured to project a first laser light for irradiating an area proximate to the port, wherein the first laser light is configured to cut collagen fibers of vitreous material aspirated through the port, the one or more optical fibers further configured to project a second laser light wherein the second laser light is configured to cauterize bleeding in an intraocular space of a patient, wherein the window is configured to allow the second laser light to pass through the window and prevent the first laser light from passing through the window.

10. The surgical instrument of claim 9, wherein the one or more optical fibers comprise a single optical fiber configured to project the first laser light and the second laser light.

11. The surgical instrument of claim 10, wherein the window is coated in a filtering film configured to allow the second laser light to pass through the distal tip and prevent the first laser light from passing through the distal tip.

12. The surgical instrument of claim 9, wherein the one or more optical fibers comprise a first optical fiber configured to project the first laser light and a second optical fiber configured to project the second laser light.

13. The surgical instrument of claim 12, wherein the probe further comprises a distal endface disposed at the distal tip, and wherein the window forms a portion of the distal endface that is aligned with the second optical fiber such that the distal endface enables the second laser light to pass through the distal tip and prevents the first laser light from passing through the distal tip.

14. The surgical instrument of claim 12, wherein the window is coated in a filtering film configured to allow the second laser light to pass through the distal tip and prevent the first laser light from passing through the distal tip.

15. The surgical instrument of claim 12, wherein a portion of the window aligned with the first optical fiber is coated in an opaque film configured to prevent the first laser light and the second laser light from passing through the distal tip.

16. The surgical instrument of claim 1, further comprising a first laser source operably coupled to the one or more optical fibers and configured to generate the first laser light configured to cut collagen fibers of vitreous material, and a second laser source operably coupled to the one or more optical fibers and configured to generate the second laser light configured to cause cauterization of a bleeding site within an eye.

17. The surgical instrument of claim 16, wherein the second laser light is a green laser light having a pulse rate within a range of 10 kilohertz and 500 kilohertz.

18. The surgical instrument of claim 9, further comprising a first laser source operably coupled to the one or more optical fibers and configured to generate the first laser light configured to cut collagen fibers of vitreous material, and a second laser source operably coupled to the one or more optical fibers and configured to generate the second laser light configured to cause cauterization of a bleeding site within an eye.

19. The surgical instrument of claim 18, wherein the second laser light is a green laser light having a pulse rate within a range of 10 kilohertz and 500 kilohertz.

\* \* \* \* \*